United States Patent
Kharas

(10) Patent No.: US 11,027,264 B2
(45) Date of Patent: Jun. 8, 2021

(54) FLUID CATALYTIC CRACKING CATALYSTS FOR INCREASING BUTYLENE YIELDS

(71) Applicant: BASF Corporation, Florham Park, NJ (US)

(72) Inventor: Karl C. Kharas, Iselin, NJ (US)

(73) Assignee: BASF Corporation, Florham Park, NJ (US)

( * ) Notice: Subject to any disclaimer, the term of this patent is extended or adjusted under 35 U.S.C. 154(b) by 0 days.

(21) Appl. No.: 16/701,371

(22) Filed: Dec. 3, 2019

(65) Prior Publication Data

US 2020/0101448 A1   Apr. 2, 2020

Related U.S. Application Data

(63) Continuation of application No. 15/778,327, filed as application No. PCT/US2016/062850 on Nov. 18, 2016, now Pat. No. 10,507,460.

(60) Provisional application No. 62/259,368, filed on Nov. 24, 2015.

(51) Int. Cl.
| | |
|---|---|
| *B01J 29/06* | (2006.01) |
| *B01J 29/08* | (2006.01) |
| *B01J 37/30* | (2006.01) |
| *B01J 37/10* | (2006.01) |
| *B01J 35/02* | (2006.01) |
| *B01J 35/00* | (2006.01) |
| *C01B 39/54* | (2006.01) |
| *C01B 39/02* | (2006.01) |
| *B01J 35/08* | (2006.01) |
| *C10G 11/05* | (2006.01) |
| *C10G 11/18* | (2006.01) |
| *B01J 37/02* | (2006.01) |
| *B01J 23/02* | (2006.01) |

(52) U.S. Cl.
CPC .......... *B01J 29/084* (2013.01); *B01J 29/088* (2013.01); *B01J 35/002* (2013.01); *B01J 35/0006* (2013.01); *B01J 35/023* (2013.01); *B01J 35/026* (2013.01); *B01J 35/08* (2013.01); *B01J 37/0246* (2013.01); *B01J 37/10* (2013.01); *B01J 37/30* (2013.01); *C01B 39/02* (2013.01); *C01B 39/54* (2013.01); *C10G 11/05* (2013.01); *C10G 11/18* (2013.01); *B01J 23/02* (2013.01); *B01J 37/0201* (2013.01); *B01J 2229/186* (2013.01); *B01J 2229/20* (2013.01); *B01J 2229/36* (2013.01); *B01J 2229/37* (2013.01); *B01J 2229/64* (2013.01); *C07C 2529/08* (2013.01); *C07C 2529/85* (2013.01)

(58) Field of Classification Search
CPC .... B01J 29/084; B01J 29/088; B01J 2229/64; B01J 2229/20; B01J 2229/186; B01J 2229/36; B01J 2229/37; B01J 35/08; B01J 35/002; B01J 35/026; B01J 35/023; B01J 35/0006; B01J 37/30; B01J 37/10; B01J 37/0201; B01J 37/0246; B01J 23/02; C07C 2529/08
USPC ............ 502/8, 9, 10, 60, 63, 64, 79, 85, 86
See application file for complete search history.

(56) References Cited

U.S. PATENT DOCUMENTS

| | | | | |
|---|---|---|---|---|
| 3,433,587 | A | * | 3/1969 | Dzierzanowski ...... C10G 11/05 423/710 |
| 4,493,902 | A | | 1/1985 | Brown et al. |
| 5,243,121 | A | | 9/1993 | Madon et al. |
| 5,576,258 | A | | 11/1996 | Chamberlain et al. |
| 5,868,818 | A | | 2/1999 | Ogawa et al. |
| 5,951,850 | A | | 9/1999 | Ino et al. |
| 6,159,887 | A | | 12/2000 | Trujillo et al. |
| 6,656,347 | B2 | | 12/2003 | Stockwell et al. |
| 6,696,378 | B2 | * | 2/2004 | Gibson ................. B01J 29/084 502/64 |
| 6,942,784 | B2 | | 9/2005 | Stockwell et al. |
| 8,609,567 | B2 | | 12/2013 | Voskoboynikov et al. |
| 2002/0179492 | A1 | | 12/2002 | Zhao et al. |
| 2004/0220046 | A1 | | 11/2004 | Stockwell et al. |
| 2007/0209969 | A1 | | 9/2007 | Shen et al. |

FOREIGN PATENT DOCUMENTS

| | | |
|---|---|---|
| CN | 1566275 A | 1/2005 |
| EP | 0 194 536 A2 | 9/1986 |
| JP | H0275697 A | 3/1990 |
| WO | 0224329 A2 | 3/2002 |

OTHER PUBLICATIONS

Cleetus, Christine et al. "Synthesis of petroleum-based fuel from waste plastics and performance analysis in a CI engine," Journal of Energy (2013).
Extended European Search Report in EP Application No. 16869112.9, dated Jul. 22, 2019. (8 pages).
International Search Report & Written Opinion in International Application No. PCT/US2016/062850, dated Mar. 3, 2017.
Noda et al., "Combined study of IRMS-TPD measurement and DFT calculation on Bronsted acidity and catalytic cracking activity of cation-exchanged Y zeolites," Journal of Catalysis, vol. 259, Issue 2, Oct. 25, 2008, pp. 203-210.
Notice of Allowance in U.S. Appl. No. 15/778,327 dated Aug. 15, 2019.
Seddigi, Z.S., "Studying the Effect of Barium Modification on the Acidic Properties of Ultrastable HY Zeolite," Energy & Fuels 2009, 23, 46-50.
Seff, Karl et al., "Three Crystal Structures of Vacuum-Dehydrated Zeolite X, $M_{46}Si_{100}Al_{92}O_{384}$, M=$Mg^{2+}$,$Ca^{2+}$, and $Ba^{2+}$," J. Phys. Chem. B (1997), 101, 6914-6920.

* cited by examiner

*Primary Examiner* — Elizabeth D Wood
(74) *Attorney, Agent, or Firm* — Lowenstein Sandler LLP

(57) ABSTRACT

A microspherical fluid catalytic cracking catalyst includes zeolite, and alkali metal ion or alkaline earth metal ion.

21 Claims, 6 Drawing Sheets

FLUID CATALYTIC CRACKING CATALYSTS FOR INCREASING BUTYLENE YIELDS

CROSS-REFERENCE TO RELATED APPLICATIONS

This application is a continuation application of U.S. patent application Ser. No. 15/778,327, filed on May 23, 2018, now U.S. Pat. No. 10,507,460, which is a U.S. National Phase Application under 35 U.S.C. § 371 of International Application No. PCT/US2016/062850, filed on Nov. 18, 2016, which in turn claims the benefit of priority to U.S. Provisional Application No. 62/259,368, filed Nov. 24, 2015, the entireties of which are incorporated herein by reference.

FIELD

The present technology is generally related to petroleum refining catalysts. More specifically, the technology is related to microspherical fluid catalytic cracking (FCC) catalysts including zeolite, and alkali metal ion or alkaline earth metal ion, and methods of preparing and using such catalysts.

SUMMARY

In one aspect, disclosed herein are microspherical fluid catalytic cracking catalysts that include a Y-zeolite and barium ion.

In another aspect, disclosed herein are microspherical catalysts including about 3.3 wt. % barium ion, wherein the catalysts have a phase composition including about 18 wt. % Y-zeolite, about 30 wt. % mullite, about 2 wt. % anatase, and about 50 wt. % amorphous material.

In another aspect, disclosed herein are methods of making a microspherical fluid catalytic cracking catalyst including the steps of: (a) mixing microspheres with a barium solution; and (b) calcining the microspheres of step (a); wherein the microspheres include Y-zeolite crystallized as a layer on the surface of a porous alumina-containing matrix.

DETAILED DESCRIPTION

Figure 1:
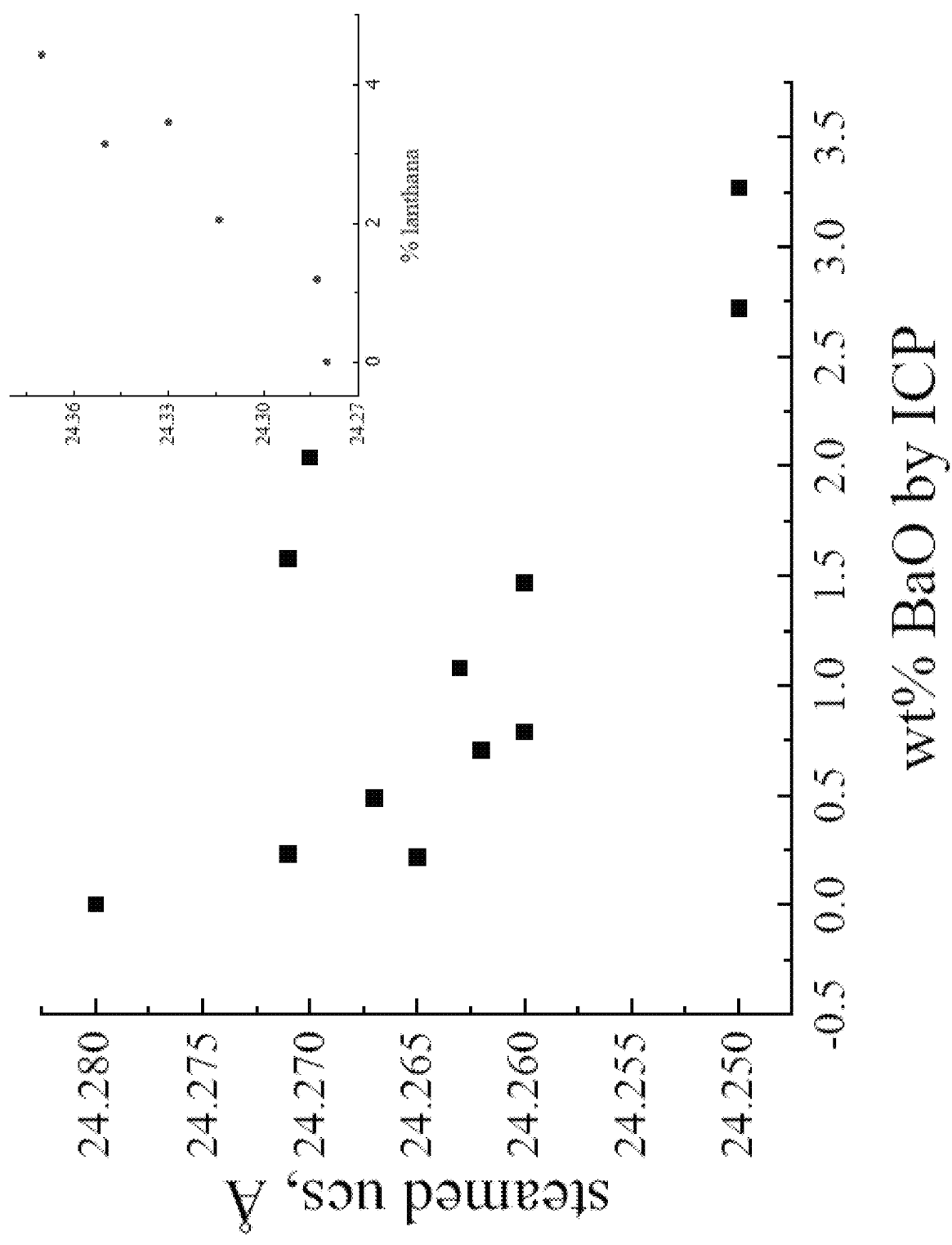
FIG. 1 illustrates unit cell size of steamed Y-zeolite as a function of barium content in barium-containing catalyst or, in inset graph, as a function of lanthanum content in lanthanum-containing catalyst.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

Fluid Catalytic Cracking

Catalytic cracking, and particularly fluid catalytic cracking (FCC), is routinely used to convert heavy hydrocarbon feedstocks to lighter products, such as gasoline and distillate range fractions. There is, however, an increasing need to enhance the yield of light olefins in the product slate from catalytic cracking processes. Light olefins (C2-C4 olefins) are important feedstocks for the petrochemical industry. Butylene, for example, a light olefin hydrocarbon with four carbon atoms per molecule, is an important chemical for use in the production of other useful materials, such as alkylate gasoline.

To produce light olefins, the catalytic cracking of heavy hydrocarbon feedstocks, such as naphtha, is typically carried out by contacting a naphtha-containing feed with a catalyst composition usually comprised of one or more crystalline microporous molecular sieves to selectively convert the feed into an olefin-containing mixture. Although various naphtha catalytic cracking processes have been proposed in the past, many of the processes do not produce commercially important light olefins, e.g., butylene, with sufficient selectivity or yield. In contrast, a practical and economic naphtha catalytic cracking process should selectively produce increased amounts of light olefins, e.g., butylene, while producing minimal amounts of methane, aromatics, and coke.

In FCC processes, a hydrocarbon feedstock is injected into the riser section of an FCC reactor, where the feedstock is cracked into lighter, more valuable products upon contacting hot catalyst circulated to the riser-reactor from a catalyst regenerator. A major breakthrough in FCC catalysts came in the early 1960s, with the introduction of molecular sieves or zeolites. These materials were incorporated into the matrix of amorphous and/or amorphous/kaolin materials constituting the FCC catalysts of that time. These new zeolitic catalysts, containing a crystalline aluminosilicate zeolite in an amorphous or amorphous/kaolin matrix of silica, alumina, silica-alumina, kaolin, clay or the like were at least 1,000-10,000 times more active for cracking hydrocarbons than the earlier amorphous or amorphous/kaolin containing silica-alumina catalysts. The introduction of zeolitic cracking catalysts revolutionized the fluid catalytic cracking process. New processes were developed to handle these high activities, such as riser cracking, shortened contact times, new regeneration processes, new improved zeolitic catalyst developments, and the like.

The zeolites typically used in FCC are crystalline aluminosilicates which have a uniform crystal structure characterized by a large number of regular small cavities interconnected by a large number of even smaller channels. It was discovered that, by virtue of this structure consisting of a network of interconnected uniformly sized cavities and channels, crystalline zeolites are able to accept, for absorption, molecules having sizes below a certain well defined value while rejecting molecules of larger sizes, and for this reason they have come to be known as "molecular sieves." This characteristic structure also gives them catalytic properties, especially for certain types of hydrocarbon conversions.

In current commercial practice, most FCC cracking catalysts used throughout the world are made of a catalytically active component large-pore zeolite. Conventional large-pore molecular sieves include zeolite X; REX; zeolite Y (or Y-zeolite); Ultrastable Y (USY); Rare Earth exchanged Y (REY); Rare Earth exchanged USY (REUSY); Dealuminated Y (DeAl Y); Ultrahydrophobic Y (UHPY); and/or dealuminated silicon-enriched zeolites, e.g., LZ-210. ZSM-20, zeolite L and naturally occurring zeolites such as faujasite, mordenite and the like have also been used.

Present Technology

It has been unexpectedly found that alkali metal or alkaline earth metal exchange, instead of lanthanum exchange, into zeolite yields a catalyst with improved butylene selectivity, lower coke production, lower hydride transfer tendency, and higher fraction of butylenes in liquefied petroleum gas (LPG).

Accordingly, disclosed herein, in one aspect, are microspherical FCC catalysts that include zeolite, and alkali metal ion or alkaline earth metal ion. Also disclosed herein are methods to prepare such FCC catalysts and methods of their use. In some embodiments, alkali metal ion or alkaline earth metal ion is selected from cesium ion and barium ion. In some embodiments, the zeolite comprises Y-zeolite. In some embodiments, the microspherical FCC catalysts include Y-zeolite and barium ion.

Zeolite includes, but is not limited to, Y-zeolite, Ultrastable Y, Dealuminated Y (DeAl Y), Ultrahydrophobic Y (UHPY), dealuminated silicon-enriched zeolites (e.g., LZ-210), ZSM-20, zeolite L, naturally occurring zeolites (e.g., faujasite, mordenite and the like), and others that are known to those skilled in the art, and any combination thereof.

The FCC catalyst has a phase composition that may include at least 5 wt. % of zeolite. In some embodiments, the FCC catalyst has a phase composition including at least 10 wt. % zeolite. In some embodiments, the FCC catalyst has a phase composition including at least 15 wt. % zeolite. In some embodiments, the FCC catalyst has a phase composition including at least 16 wt. % zeolite. In some embodiments, the FCC catalyst has a phase composition including at least 17 wt. % zeolite. In some embodiments, the FCC catalyst has a phase composition including at least 18 wt. % zeolite. In some embodiments, the FCC catalyst has a phase composition including at least 19 wt. % zeolite. In some embodiments, the FCC catalyst has a phase composition including at least 20 wt. % zeolite. In some embodiments, the FCC catalyst has a phase composition including at least 25 wt. % zeolite. In some embodiments, the FCC catalyst has a phase composition including at least 30 wt. % zeolite. In some embodiments, the FCC catalyst has a phase composition including at least 35 wt. % zeolite. In some embodiments, the FCC catalyst has a phase composition including at least 40 wt. % zeolite. In some embodiments, the FCC catalyst has a phase composition including at least 45 wt. % zeolite. In some embodiments, the FCC catalyst has a phase composition including at least 50 wt. % zeolite. In some embodiments, the FCC catalyst has a phase composition including at least 55 wt. % zeolite. In some embodiments, the FCC catalyst has a phase composition including at least 60 wt. % zeolite. In some embodiments, the FCC catalyst has a phase composition including at least 65 wt. % zeolite. In some embodiments, the FCC catalyst has a phase composition including at least 70 wt. % zeolite. In some embodiments, the FCC catalyst has a phase composition including about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 wt. %, including increments therein, of zeolite. In some embodiments, the FCC catalyst has a phase composition including from about 5 wt. % to about 25 wt. % zeolite. In some embodiments, the FCC catalyst has a phase composition including from about 10 wt. % to about 20 wt. % zeolite. In some embodiments, the FCC catalyst has a phase composition including from about 10 wt. % to about 35 wt. % zeolite. In some embodiments, the FCC catalyst has a phase composition including from about 10 wt. % to about 50 wt. % zeolite.

The FCC catalyst has a phase composition that may include at least 5 wt. % of Y-zeolite. In some embodiments, the FCC catalyst has a phase composition including at least 10 wt. % Y-zeolite. In some embodiments, the FCC catalyst has a phase composition including at least 15 wt. % Y-zeolite. In some embodiments, the FCC catalyst has a phase composition including at least 16 wt. % Y-zeolite. In some embodiments, the FCC catalyst has a phase composition including at least 17 wt. % Y-zeolite. In some embodiments, the FCC catalyst has a phase composition including at least 18 wt. % Y-zeolite. In some embodiments, the FCC catalyst has a phase composition including at least 19 wt. % Y-zeolite. In some embodiments, the FCC catalyst has a phase composition including at least 20 wt. % Y-zeolite. In some embodiments, the FCC catalyst has a phase composition including at least 25 wt. % Y-zeolite. In some embodiments, the FCC catalyst has a phase composition including at least 30 wt. % Y-zeolite. In some embodiments, the FCC catalyst has a phase composition including at least 35 wt. % Y-zeolite. In some embodiments, the FCC catalyst has a phase composition including at least 40 wt. % Y-zeolite. In some embodiments, the FCC catalyst has a phase composition including at least 45 wt. % Y-zeolite. In some embodiments, the FCC catalyst has a phase composition including at least 50 wt. % Y-zeolite. In some embodiments, the FCC catalyst has a phase composition including at least 55 wt. % Y-zeolite. In some embodiments, the FCC catalyst has a phase composition including at least 60 wt. % Y-zeolite. In some embodiments, the FCC catalyst has a phase composition including at least 65 wt. % Y-zeolite. In some embodiments, the FCC catalyst has a phase composition including at least 70 wt. % Y-zeolite. In some embodiments, the FCC catalyst has a phase composition including about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 wt. %, including increments therein, of Y-zeolite. In some embodiments, the FCC catalyst has a phase composition including from about 5 wt. % to about 25 wt. % Y-zeolite. In some embodiments, the FCC catalyst has a phase composition including from about 10 wt. % to about 20 wt. % Y-zeolite. In some embodiments, the FCC catalyst has a phase composition including from about 10 wt. % to about 35 wt. % Y-zeolite. In some embodiments, the FCC catalyst has a phase composition including from about 10 wt. % to about 50 wt. % Y-zeolite.

The FCC catalyst has a phase composition that may also include an amorphous material. Illustrative amorphous materials include, but are not limited to, silica-alumina. In further embodiments, the amorphous material may be derived from the disintegration of crystalline zeolite. In still further embodiments, the amorphous material may be derived from the disintegration of crystalline Y-zeolite.

The FCC catalyst may have a phase composition further including at least about 30 wt. % amorphous material. In some embodiments, the phase composition further includes at least about 35 wt. % amorphous material. In some embodiments, the phase composition further includes at least about 40 wt. % amorphous material. In some embodiments, the phase composition further includes at least about 45 wt. % amorphous material. In some embodiments, the phase composition further includes at least about 50 wt. % amorphous material. In some embodiments, the phase composition further includes at least about 55 wt. % amorphous material. In some embodiments, the phase composition further includes about 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95 wt. %, including increments therein, of amorphous material. In some embodiments, the phase composition further includes from about 25 wt. % to about 55 wt. % amorphous material. In some embodiments, the phase composition further includes from about 25 wt. % to about 50 wt. % amorphous material. In some embodiments, the phase composition further includes from about 30 wt. % to about 50 wt. % amorphous material. In some embodiments, the phase composition further includes from about 35 wt. % to about 50 wt. % amorphous material. In some embodiments, the phase composition further includes from about 35 wt. % to about 75 wt. % amorphous material. In some embodiments, the phase composition further includes from about 35 wt. % to about 95 wt. % amorphous material.

The FCC catalyst has a phase composition that may further include mullite. In some embodiments, the phase composition further includes at least about 20 wt. % mullite. In some embodiments, the phase composition further includes at least about 25 wt. % mullite. In some embodiments, the phase composition further includes at least about 30 wt. % mullite. In some embodiments, the phase composition further includes at least about 35 wt. % mullite. In some embodiments, the phase composition further includes about 20, 21, 22, 23, 24, 25, 26, 27, 28, 29, 30, 31, 32, 33, 34, 35 wt. %, including increments therein, of mullite. In some embodiments, the phase composition further includes from about 20 wt. % to about 35 wt. % mullite. In some embodiments, the phase composition further includes from about 20 wt. % to about 30 wt. % mullite. In some embodiments, the phase composition further includes from about 25 wt. % to about 35 wt. % mullite.

The FCC catalyst has a phase composition may further include anatase. In some embodiments, the phase composition further includes at least about 0.5 wt. % anatase. In some embodiments, the phase composition further includes at least about 1.0 wt. % anatase. In some embodiments, the phase composition further includes at least about 1.5 wt. % anatase. In some embodiments, the phase composition further includes at least about 2.0 wt. % anatase. In some embodiments, the phase composition further includes at least about 2.5 wt. % anatase. In some embodiments, the phase composition further includes at least about 3.0 wt. % anatase. In some embodiments, the phase composition further includes about 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.5, 4.0, 4.5, 5.0, 5.5, 6.0, 6.5, 7.0, 7.5, 8.0, 8.5, 9.0, 9.5, or 10 wt. %, including increments therein, of anatase. In some embodiments, the phase composition further includes from about 0.5 wt. % to about 5.0 wt. % of anatase. In some embodiments, the phase composition further includes from about 0.5 wt. % to about 4.0 wt. % of anatase. In some embodiments, the phase composition further includes from about 0.5 wt. % to about 3.0 wt. % of anatase. In some embodiments, the phase composition further includes from about 1.0 wt. % to about 5.0 wt. % of anatase. In some embodiments, the phase composition further includes from about 1.0 wt. % to about 4.0 wt. % of anatase. In some embodiments, the phase composition further includes from about 1.0 wt. % to about 3.0 wt. % of anatase. In some embodiments, the phase composition further includes from about 1.0 wt. % to about 2.0 wt. % of anatase.

The FCC catalyst may have a phase composition including zeolite, mullite, and amorphous material. In some embodiments, the FCC catalyst has a phase composition including zeolite, mullite, anatase, and amorphous material.

The FCC catalyst may have a phase composition including Y-zeolite, mullite, and amorphous material. In some embodiments, the FCC catalyst has a phase composition including Y-zeolite, mullite, anatase, and amorphous material.

The FCC catalyst average particle size may be from about 60 to about 100 micrometers. In some embodiments, the FCC catalyst has an average particle size of about 60 to about 90 micrometers. In some embodiments, the FCC catalyst has an average particle size of about 60 to about 80 micrometers. In some embodiments, the FCC catalyst has an average particle size of about 60 to about 70 micrometers. In some embodiments, the FCC catalyst has an average particle size of about 80 to about 100 micrometers. In some embodiments, the FCC catalyst has an average particle size of about 70 to about 90 micrometers. In some embodiments, the FCC catalyst has an average particle size of about 70 to about 100 micrometers. In some embodiments, the FCC catalyst has an average particle size of about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 micrometers.

In some embodiments, the zeolite is incorporated into an amorphous binder. In some embodiments, the zeolite is Y-zeolite. Suitable binders include, but are not limited to, silica, silica-alumina, alumina, clay (e.g., kaolin) or other known inorganic binders. In some embodiments, a transitional alumina, such as $\gamma$-$Al_2O_3$, $\eta$-$Al_2O_3$, $\delta$-$Al_2O_3$, $\theta$-$Al_2O_3$, $\kappa$-$Al_2O_3$ or any combination thereof, is included in the composition. In some embodiments, a slurry containing zeolite and one or more binders is made and spray-dried to yield microspheres whose average particle size is from about 60 to about 100 micrometers. In some embodiments, the slurry further contains alumina. In some embodiments, the slurry further contains clay. In some embodiments, the slurry further contains alumina and clay. Any effective binder may be used; particularly effective binders include, but are not limited to, aluminum chlohydrol sol, silica sol, and aluminum phosphates.

The Y-zeolite may be produced into high zeolite content microspheres by the in-situ procedure described in U.S. Pat. No. 4,493,902 ("the '902 patent"), the teachings of which are incorporated by reference in their entirety. The '902 patent discloses FCC catalysts including attrition-resistant, high zeolitic content, catalytically active microspheres containing more than about 40%, preferably 50-70% by weight Y faujasite and methods for making such catalysts by crystallizing more than about 40% sodium Y-zeolite in porous microspheres composed of a mixture of metakaolin (kaolin calcined to undergo a strong endothermic reaction associated with dehydroxylation) and kaolin calcined under conditions more severe than those used to convert kaolin to metakaolin, i.e., kaolin calcined to undergo the characteristic kaolin exothermic reaction, sometimes referred to as the spinel form of calcined kaolin. The microspheres containing the two forms of calcined kaolin could also be immersed in an alkaline sodium silicate solution, which is heated, preferably until the maximum obtainable amount of Y faujasite is crystallized in the microspheres.

In carrying out the invention described in the '902 patent, the microspheres composed of kaolin calcined to undergo the exotherm and metakaolin are reacted with a caustic enriched sodium silicate solution in the presence of a crystallization initiator (seeds) to convert silica and alumina in the microspheres into synthetic sodium faujasite (Y-zeolite). The microspheres are separated from the sodium silicate mother liquor, ion-exchanged with rare earth, ammonium ions or both to form rare earth or various known stabilized forms of catalysts. The technology of the '902 patent provides means for achieving a desirable and unique combination of high zeolite content associated with high activity, good selectivity and thermal stability, as well as attrition-resistance.

In some embodiments, the synthetic sodium faujasite of the '902 patent undergoes barium ion-exchange to form the Y-zeolite of the FCC catalyst of the present invention.

The Y-zeolite may be produced as zeolite microspheres, known as the NAPHTHAMAX® catalyst from BASF, which are disclosed in U.S. Pat. No. 6,656,347 ("the '347 patent") and U.S. Pat. No. 6,942,784 ("the '784 patent"), both of which are incorporated by reference herein in their entirety. These zeolite microspheres are macroporous, have sufficient levels of zeolite to be very active and are of a unique morphology to achieve effective conversion of hydrocarbons to cracked gasoline products with improved bottoms cracking under short contact time FCC processing. These zeolite microspheres are produced by novel processing, which is a modification of technology described in the '902 patent. It had been found that if the non-zeolite, alumina-rich matrix of the catalyst was derived from an ultrafine hydrous kaolin source having a particulate size such that 90 wt. % of the hydrous kaolin particles were less than 2 microns, and which was pulverized and calcined through the exotherm, then a macroporous zeolite microsphere was produced. More generally, the FCC catalyst matrix useful to achieve FCC catalyst macroporosity was derived from alumina sources, such as kaolin calcined through the exotherm, that have a specified water pore volume, which distinguished over prior art calcined kaolin used to form the catalyst matrix. The water pore volume was derived from an Incipient Slurry Point (ISP) test, which is described in the patent.

The morphology of the microsphere catalysts of '347 patent and the '784 patent which were formed is unique relative to the in-situ microsphere catalysts formed previously. Use of a pulverized, ultrafine hydrous kaolin calcined through the exotherm yields in-situ zeolite microspheres having a macroporous structure in which the macropores of the structure are essentially coated or lined with zeolite subsequent to crystallization. Macroporosity as defined herein means the catalyst has a macropore volume in the pore range of 600-20,000 angstroms of at least 0.07 cc/gm mercury intrusion, preferably at least 0.10 cc/gm mercury intrusion. This catalyst is optimal for FCC processing, including the short contact time processing in which the hydrocarbon feed is contacted with a catalyst for times of about 3 seconds or less.

In the broadest sense, NAPHTHAMAX® as described in the '347 patent and the '784 patent is not restricted to macroporous catalysts having a non-zeolite matrix derived solely from kaolin. Thus, any alumina source which has the proper combinations of porosity and reactivity during zeolite synthesis and can generate the desired catalyst macroporosity and morphology can be used. The desired morphology includes a matrix which is well dispersed throughout the catalyst, and the macropore walls of matrix are lined with zeolite and are substantially free of binder coatings. Accordingly, not only is the large pore surface area of the catalyst vastly improved over previous catalysts, and the active matrix dispersed throughout the microsphere, the zeolite crystals are readily accessible to the hydrocarbon feed. While not wishing to be bound by any theory of operation, it appears that previous catalysts in which the zeolite is incorporated into a matrix by physical mixing and glued with binder have sufficient macroporosity; however, the binder coats the active zeolite catalyst thereby blocking accessibility thereto. The NAPHTHAMAX® microsphere catalysts have a morphology which allows fast diffusion into the catalyst due to the macroporosity and enhanced dispersion of the matrix, and further provides the highest accessibility to the zeolite inasmuch as the zeolite is freely coated onto the walls of the pores. The term "freely" means that the zeolite phase is present on the surface of the matrix and is unobstructed by any binder phases. Merely having macroporosity does not provide the results that have been obtained, since conventional incorporated catalysts have similar macroporosity. It is therefore the combination of porosity and zeolite-coated macropore walls that give the surprising selectivity results.

In some embodiments, the FCC catalyst includes an alkali metal ion-exchanged zeolite. In some embodiments, the FCC catalyst includes a cesium-exchanged zeolite. In some embodiments, the FCC catalyst includes a cesium-exchanged zeolite crystallized in-situ in a porous kaolin matrix. In some embodiments, the zeolite is crystallized as a layer on the surface of a porous alumina-containing matrix.

In further embodiments, the matrix is derived from a kaolin calcined through the exotherm.

In some embodiments, the FCC catalyst includes an alkali metal ion-exchanged Y-zeolite. In some embodiments, the FCC catalyst includes a cesium-exchanged Y-zeolite. In some embodiments, the FCC catalyst includes a cesium-exchanged Y-zeolite crystallized in-situ in a porous kaolin matrix. In some embodiments, the Y-zeolite is crystallized as a layer on the surface of a porous alumina-containing matrix. In further embodiments, the matrix is derived from a kaolin calcined through the exotherm.

In some embodiments, the FCC catalyst includes at least about 0.3 wt. % cesium ion. In some embodiments, the FCC catalyst includes at least about 0.4 wt. % cesium ion. In some embodiments, the FCC catalyst includes at least about 0.5 wt. % cesium ion. In some embodiments, the FCC catalyst includes at least about 0.6 wt. % cesium ion. In some embodiments, the FCC catalyst includes at least about 0.7 wt. % cesium ion. In some embodiments, the FCC catalyst includes at least about 0.8 wt. % cesium ion. In some embodiments, the FCC catalyst includes at least about 0.9 wt. % cesium ion. In some embodiments, the FCC catalyst includes at least about 1 wt. % cesium ion. In some embodiments, the FCC catalyst includes at least about 2 wt. % cesium ion. In some embodiments, the FCC catalyst includes at least about 3 wt. % cesium ion. In some embodiments, the FCC catalyst includes at least about 4 wt. % cesium ion. In some embodiments, the FCC catalyst includes at least about 5 wt. % cesium ion. In some embodiments, the FCC catalyst includes about 0.3, 0.4, 0.5, 0.6, 0.7, 0.8, 0.9, 1, 2, 3, 4, 5, 6, 7, 8, 9, or 10 wt. %, including increments therein, of cesium ion. In some embodiments, the FCC catalyst includes from about 0.3 wt. % to about 5 wt. % cesium ion. In some embodiments, the FCC catalyst includes from about 2 wt. % to about 5 wt. % cesium ion. In some embodiments, the FCC catalyst includes from about 2 wt. % to about 4 wt. % cesium ion.

In some embodiments, the FCC catalyst includes an alkaline earth metal ion-exchanged Y-zeolite. In some embodiments, the FCC catalyst includes a barium-exchanged Y-zeolite. In some embodiments, the FCC catalyst includes a barium-exchanged Y-zeolite crystallized in-situ in a porous kaolin matrix. In some embodiments, the Y-zeolite is crystallized as a layer on the surface of a porous alumina-containing matrix. In further embodiments, the matrix is derived from a kaolin calcined through the exotherm.

The Y-zeolite unit cell may include barium ion at the ion exchange site III. The multiplicity of site III is 96. In some embodiments, the Y-zeolite unit cell includes about 0.5 to 10 barium atoms at the ion exchange site III. In some embodiments, the Y-zeolite unit cell includes about 4 barium atoms at the ion exchange site III. In some embodiments, the barium ions do not occupy ion exchange sites I' and II' of the Y-zeolite unit cell. In some embodiments, the Y-zeolite unit cell includes barium ion at the ion exchange site III and barium ions do not occupy ion exchange sites I' and II'.

In some embodiments, no more than about half of the barium ions can be located on the zeolite by x-ray diffraction. In some embodiments, no more than about half of the barium ions can be located on the Y-zeolite by x-ray diffraction.

In some embodiments, the FCC catalyst includes at least about 0.3 wt. % barium ion. In some embodiments, the FCC catalyst includes at least about 0.4 wt. % barium ion. In some embodiments, the FCC catalyst includes at least about 0.5 wt. % barium ion. In some embodiments, the FCC catalyst includes at least about 0.6 wt. % barium ion. In some embodiments, the FCC catalyst includes at least about 0.7 wt. % barium ion. In some embodiments, the FCC catalyst includes at least about 0.8 wt. % barium ion. In some embodiments, the FCC catalyst includes at least about 0.9 wt. % barium ion. In some embodiments, the FCC catalyst includes at least about 1 wt. % barium ion. In some embodiments, the FCC catalyst includes at least about 2 wt. % barium ion. In some embodiments, the FCC catalyst includes at least about 3 wt. % barium ion. In some embodiments, the FCC catalyst includes at least about 4 wt. % barium ion. In some embodiments, the FCC catalyst includes at least about 5 wt. % barium ion. In some embodiments, the FCC catalyst includes about 0.3, 0.4, 0.5, 0.6, 0.7, 0.8, 0.9, 1, 2, 3, 4, 5, 6, 7, 8, 9, or 10 wt. %, including increments therein, of barium ion. In some embodiments, the FCC catalyst includes from about 0.3 wt. % to about 5 wt. % barium ion. In some embodiments, the FCC catalyst includes from about 2 wt. % to about 5 wt. % barium ion. In some embodiments, the FCC catalyst includes from about 2 wt. % to about 4 wt. % barium ion.

In some embodiments, the Y-zeolite has a unit cell parameter of less than or equal to 24.70 Å. In some embodiments, the Y-zeolite has a unit cell parameter of less than or equal to 24.60 Å. In some embodiments, the Y-zeolite has a unit cell parameter of less than or equal to 24.55 Å. In some embodiments, the Y-zeolite has a unit cell parameter of from about 24.10 Å to about 24.70 Å. In some embodiments, the Y-zeolite has a unit cell parameter of from about 24.10 Å to about 24.65 Å. In some embodiments, the Y-zeolite has a unit cell parameter of from about 24.10 Å to about 24.60 Å. In some embodiments, the Y-zeolite has a unit cell parameter of from about 24.10 Å to about 24.55 Å. In some embodiments, the Y-zeolite has a unit cell parameter of from about 24.10 Å to about 24.54 Å. In some embodiments, the Y-zeolite has a unit cell parameter of from about 24.10 Å to about 24.53 Å. In some embodiments, the Y-zeolite has a unit cell parameter of from about 24.10 Å to about 24.52 Å. In some embodiments, the Y-zeolite has a unit cell parameter of from about 24.10 Å to about 24.51 Å. In some embodiments, the Y-zeolite has a unit cell parameter of from about 24.20 Å to about 24.55 Å. In some embodiments, the Y-zeolite has a unit cell parameter of from about 24.20 Å to about 24.54 Å. In some embodiments, the Y-zeolite has a unit cell parameter of from about 24.20 Å to about 24.53 Å. In some embodiments, the Y-zeolite has a unit cell parameter of from about 24.20 Å to about 24.52 Å. In some embodiments, the Y-zeolite has a unit cell parameter of from about 24.20 Å to about 24.51 Å. In some embodiments, the Y-zeolite has a unit cell parameter of from about 24.30 Å to about 24.55 Å. In some embodiments, the Y-zeolite has a unit cell parameter of from about 24.30 Å to about 24.54 Å. In some embodiments, the Y-zeolite has a unit cell parameter of from about 24.30 Å to about 24.53 Å. In some embodiments, the Y-zeolite has a unit cell parameter of from about 24.30 Å to about 24.52 Å. In some embodiments, the Y-zeolite has a unit cell parameter of from about 24.30 Å to about 24.51 Å. In some embodiments, the Y-zeolite has a unit cell parameter of from about 24.40 Å to about 24.55 Å. In some embodiments, the Y-zeolite has a unit cell parameter of from about 24.40 Å to about 24.54 Å. In some embodiments, the Y-zeolite has a unit cell parameter of from about 24.40 Å to about 24.53 Å. In some embodiments, the Y-zeolite has a unit cell parameter of from about 24.40 Å to about 24.52 Å. In some embodiments, the Y-zeolite has a unit cell parameter of from about 24.40 Å to about 24.51 Å. In some embodiments, the Y-zeolite has a unit cell parameter of from about 24.45 Å to about 24.55 Å. In some embodiments, the Y-zeolite has a unit cell parameter of from about 24.45 Å to about 24.54 Å. In some embodiments, the Y-zeolite has a unit cell parameter of from about 24.45 Å to about 24.53 Å. In some embodiments, the Y-zeolite has a unit cell parameter of from about 24.45 Å to about 24.52 Å. In some embodiments, the Y-zeolite has a unit cell parameter of from about 24.45 Å to about 24.51 Å. In some embodiments, the Y-zeolite has a unit cell parameter of about 24.10, 24.11, 24.12, 24.13, 24.14, 24.15, 24.16, 24.17, 24.18, 24.19, 24.20, 24.21, 24.22, 24.23, 24.24, 24.25, 24.26, 24.27, 24.28, 24.29, 24.30, 24.31, 24.32. 24.33, 24.34, 24.35, 24.36, 24.37, 24.38, 24.39, 24.40, 24.41, 24.42, 24.43, 24.44, 24.45, 24.46, 24.47, 24.48, 24.49, 24.50, 24.51, 24.52, 24.53, 24.54, 24.55, 24.56, 24.57, 24.58, 24.59, 24.60, 24.61, 24.62, 24.63, 24.64, 24.65, 24.66, 24.67, 24.68, 24.69, or 24.70 Å.

In some embodiments, disclosed herein, are microspherical catalysts including about 3.3 wt. % barium ion, wherein the catalyst has a phase composition including about 18 wt. % zeolite, about 30 wt. % mullite, about 2 wt. % anatase, and about 50 wt. % amorphous material. In some embodiments, the zeolite has a unit cell parameter of about 24.26 Å. In some embodiments, the catalyst contains about 4 barium atoms in the zeolite unit cell at ion exchange site III. In some embodiments, the fractional coordinates of ion exchange site III are x=y=0.35 and z=0.21. In some embodiments, only about half of the barium ions can be located in the zeolite by X-ray diffraction. In some embodiments, the catalyst has an average particle size of 60-80 micrometers.

In some embodiments, disclosed herein, are microspherical catalysts including about 3.3 wt. % barium ion, wherein the catalyst has a phase composition including about 18 wt. % Y-zeolite, about 30 wt. % mullite, about 2 wt. % anatase, and about 50 wt. % amorphous material. In some embodiments, the Y-zeolite has a unit cell parameter of about 24.26 Å. In some embodiments, the catalyst contains about 4 barium atoms in the Y-zeolite unit cell at ion exchange site III. In some embodiments, the fractional coordinates of ion exchange site III are x=y=0.35 and z=0.21. In some embodiments, only about half of the barium ions can be located in the zeolite by X-ray diffraction. In some embodiments, the catalyst has an average particle size of 60-80 micrometers.

In some embodiments, disclosed herein are microspherical catalysts with a phase composition consisting essentially of barium-exchanged zeolite, mullite, and amorphous material. In some embodiments, disclosed herein are microspherical catalysts with a phase composition consisting essentially of barium-exchanged zeolite, mullite, anatase, and amorphous material. In some embodiments, disclosed herein are microspherical catalysts with a phase composition consisting essentially of from about 10 wt. % to about 50 wt. % barium-exchanged zeolite, from about 20 wt. % to about 35 wt. % mullite, from about 1 wt. % to about 5 wt. % anatase, and from about 25 wt. % to about 55 wt. % amorphous material, wherein the catalysts contain from about 2 wt. % to about 10 wt. % barium ion. In some embodiments, disclosed herein are microspherical catalysts with a phase composition consisting essentially of barium-exchanged Y-zeolite, mullite, anatase, and amorphous material, wherein the zeolite is crystallized as a layer on the surface of a porous alumina-containing matrix.

In some embodiments, disclosed herein are microspherical catalysts with a phase composition consisting essentially of barium-exchanged Y-zeolite, mullite, and amorphous material. In some embodiments, disclosed herein are microspherical catalysts with a phase composition consisting essentially of barium-exchanged Y-zeolite, mullite, anatase, and amorphous material. In some embodiments, disclosed herein are microspherical catalysts with a phase composition consisting essentially of from about 10 wt. % to about 50 wt. % barium-exchanged Y-zeolite, from about 20 wt. % to about 35 wt. % mullite, from about 1 wt. % to about 5 wt. % anatase, and from about 25 wt. % to about 55 wt. % amorphous material, wherein the catalysts contain from about 2 wt. % to about 10 wt. % barium ion. In some embodiments, disclosed herein are microspherical catalysts with a phase composition consisting essentially of barium-exchanged Y-zeolite, mullite, anatase, and amorphous material, wherein the Y-zeolite is crystallized as a layer on the surface of a porous alumina-containing matrix.

Methods of Preparation

In another aspect, disclosed herein are methods of making the FCC catalysts described herein.

The method of making a microspherical fluid catalytic cracking catalyst may include mixing microspheres with a barium solution to form a barium-microsphere mixture; and calcining the barium-microsphere mixture to form a first calcined material, wherein prior to the mixing with the barium solution, the microspheres include zeolite crystallized as a layer on the surface of a porous alumina-containing matrix. In some embodiments, cesium is used in place of barium.

The method of making a microspherical fluid catalytic cracking catalyst may include mixing microspheres with a barium solution to form a barium-microsphere mixture; and calcining the barium-microsphere mixture to form a first calcined material, wherein prior to the mixing with the barium solution, the microspheres include Y-zeolite crystallized as a layer on the surface of a porous alumina-containing matrix. In some embodiments, cesium is used in place of barium.

In some embodiments, the mixing is conducted at acidic pH conditions. In some embodiments, the mixing is conducted at about, or at, pH=5. In some embodiments, the mixing is conducted at least at pH=5. In some embodiments, the mixing is conducted at about, or at, pH=4. In some embodiments, the mixing is conducted at least at pH=4. In some embodiments, the mixing is conducted at about, or at, pH=3. In some embodiments, the mixing is conducted at least at pH=3. In some embodiments, the mixing is conducted at about, or at, pH=2.5. In some embodiments, the mixing is conducted at least at pH=2.5. In some embodiments, the mixing is conducted at, or about at, pH=2. In some embodiments, the mixing is conducted at least at pH=2.

In some embodiments, the mixing is conducted at a temperature below room temperature. In some embodiments, the mixing is conducted at room temperature. In some embodiments, the mixing is conducted at a temperature above room temperature. In some embodiments, the mixing is conducted at a temperature of at least about 50° C. In some embodiments, the mixing is conducted at a temperature of at least about 60° C. In some embodiments, the mixing is conducted at a temperature of at least about 70° C. In some embodiments, the mixing is conducted at a temperature of at least about 80° C. In some embodiments, the mixing is conducted at a temperature of about 10, 15, 20, 25, 30, 35, 40, 45, 50, 55, 60, 65, 70, 75, 80, 85, 90, 95, or 100° C., including increments therein.

In some embodiments, the calcining is conducted for at least about 15 minutes. In some embodiments, the calcining is conducted for at least about 30 minutes. In some embodiments, the calcining is conducted for at least about one hour. In some embodiments, the calcining is conducted for at least about two hours. In some embodiments, the calcining is conducted for about one to about two hours. In some embodiments, the calcining is conducted for about 0.25, 0.5, 1, 2, 3, 4, or 5 hours, including increments therein.

In some embodiments, the calcining is conducted at a temperature of from about 500° C. to about 750° C. In some embodiments, the calcining is conducted at a temperature of from about 480° C. to about 740° C. In some embodiments, the calcining is conducted at a temperature of from about 500° C. to about 650° C. In some embodiments, the calcining is conducted at a temperature of from about 600° C. to about 700° C. In some embodiments, the calcining is conducted at a temperature of about 480, 500, 525, 550, 575, 600, 625, 650, 675, 700, 725, 750, 775, 800, 825, or 850° C., including increments therein.

The method may further include mixing the microspheres with an ammonium solution prior to the mixing with the barium solution, wherein the microspheres include Y-zeolite in the sodium form prior to the mixing with the ammonium solution. In some embodiments, the mixing with the ammonium solution is conducted at acidic pH conditions. In some embodiments, the mixing with the ammonium solution is conducted at pH=5. In some embodiments, the mixing with the ammonium solution is conducted at about pH=5. In some embodiments, the mixing with the ammonium solution is conducted at least at pH=5. In some embodiments, the mixing with the ammonium solution is conducted at pH=4. In some embodiments, the mixing with the ammonium solution is conducted at about pH=4. In some embodiments, the mixing with the ammonium solution is conducted at least at pH=4. In some embodiments, the mixing with the ammonium solution is conducted at pH=3. In some embodiments, the mixing with the ammonium solution is conducted at about pH=3. In some embodiments, the mixing with the ammonium solution is conducted at least at pH=3. In some embodiments, the mixing with the ammonium solution is conducted at pH=2.5. In some embodiments, the mixing with the ammonium solution is conducted at about pH=2.5. In some embodiments, the mixing with the ammonium solution is conducted at least at pH=2.5. In some embodiments, the mixing with the ammonium solution is conducted at pH=2. In some embodiments, the mixing with the ammonium solution is conducted at about pH=2. In some embodiments, the mixing with the ammonium solution is conducted at least at pH=2. In some embodiments, the mixing with the ammonium solution is conducted at a temperature above room temperature. In some embodiments, the mixing with the ammonium solution is conducted at a temperature of at least about 50° C. In some embodiments, the mixing with the ammonium solution is conducted at a temperature of at least about 60° C. In some embodiments, the mixing with the ammonium solution is conducted at a temperature of at least about 70° C. In some embodiments, the mixing with the ammonium solution is conducted at a temperature of about 50, 55, 60, 65, 70, 75, 80, 85, 90, 95, or 100° C., including increments therein. In some embodiments, a cesium solution is used in place of the barium solution.

The method may further include mixing the first calcined material with another ammonium solution to form an ammoniated material. In some embodiments, the mixing with another ammonium solution is conducted at acidic pH conditions. In some embodiments, the mixing with another ammonium solution is conducted at pH=5. In some embodiments, the mixing with another ammonium solution is conducted at about pH=5. In some embodiments, the mixing with another ammonium solution is conducted at least at pH=5. In some embodiments, the mixing with another ammonium solution is conducted at pH=4. In some embodiments, the mixing with another ammonium solution is conducted at about pH=4. In some embodiments, the mixing with another ammonium solution is conducted at least at pH=4. In some embodiments, the mixing with another ammonium solution is conducted at pH=3. In some embodiments, the mixing with another ammonium solution is conducted at about pH=3. In some embodiments, the mixing with another ammonium solution is conducted at least at pH=3. In some embodiments, the mixing with another ammonium solution is conducted at pH=2.5. In some embodiments, the mixing with another ammonium solution is conducted at about pH=2.5. In some embodiments, the mixing with another ammonium solution is conducted at least at pH=2.5. In some embodiments, the mixing with another ammonium solution is conducted at pH=2. In some embodiments, the mixing with another ammonium solution is conducted at about pH=2. In some embodiments, the mixing with another ammonium solution is conducted at least at pH=2.

In some embodiments, the mixing with an ammonium solution is conducted at a temperature below room temperature. In some embodiments, the mixing is conducted at room temperature. In some embodiments, the mixing is conducted at a temperature above room temperature. In some embodiments, the mixing is conducted at a temperature of at least about 50° C. In some embodiments, the mixing is conducted at a temperature of at least about 60° C. In some embodiments, the mixing is conducted at a temperature of at least about 70° C. In some embodiments, the mixing is conducted at a temperature of at least about 80° C. In some embodiments, the mixing is conducted at a temperature of about 10, 15, 20, 25, 30, 35, 40, 45, 50, 55, 60, 65, 70, 75, 80, 85, 90, 95, or 100° C., including increments therein.

The method may further include calcining the ammoniated material to form a second calcined material. In some embodiments, calcining the ammoniated material is conducted for at least about 15 minutes. In some embodiments, calcining the ammoniated material is conducted for at least about 30 minutes. In some embodiments, calcining the ammoniated material is conducted for at least about one hour. In some embodiments, calcining the ammoniated material is conducted for at least about two hours. In some embodiments, calcining the ammoniated material is conducted for about one to about two hours. In some embodiments, calcining the ammoniated material is conducted for about 0.25, 0.5, 0.75, 1, 2, 3, 4, or 5 hours, including increments therein. In some embodiments, calcining the ammoniated material is conducted at a temperature of from about 500° C. to about 800° C. In some embodiments, calcining the ammoniated material is conducted at a temperature of from about 500° C. to about 700° C. In some embodiments, calcining the ammoniated material is conducted at a temperature of from about 500° C. to about 600° C. In some embodiments, calcining the ammoniated material is conducted at a temperature of from about 600° C. to about 700° C. In some embodiments, calcining the ammoniated material is conducted at a temperature of about 500, 525, 550, 575, 600, 625, 650, 675, 700, 725, 750, 775, 800, 825, 850° C., including increments therein.

The method further include steam-treating. In some embodiments, the steam-treating is performed on the first calcined material. In some embodiments, the steam-treating is performed on the second calcined material. In some embodiments, the steam-treating is conducted at a temperature of at least about 600° C. In some embodiments, the steam-treating conducted at a temperature of at least about 700° C. In some embodiments, the steam-treating is conducted at a temperature of at least about 800° C. In some embodiments, the steam-treating is conducted at a temperature of from about 600° C. to about 800° C. In some embodiments, the steam-treating is conducted at a temperature of from about 600° C. to about 700° C. In some embodiments, the steam-treating is conducted at a temperature of from about 700° C. to about 800° C. In some embodiments, the steam-treating is conducted at a temperature of about 600, 625, 650, 675, 700, 725, 750, 775, 800, 825, or 850° C., including increments therein. In some embodiments, the steam-treating is conducted for at least about two hours. In some embodiments, the steam-treating is conducted for at least about three hours. In some embodiments, the steam-treating is conducted for at least about four hours. In some embodiments, the steam-treating is conducted for about one to about four hours. In some embodiments, the steam-treating is conducted for about two to about four hours. In some embodiments, the steam-treating is conducted for about 1, 2, 3, 4, 5, 6, 7, 8, 9, or 10 hours, including increments therein. In some embodiments, the final step is conducted in a fluidized bed reactor. In some embodiments, the final step is conducted in a rotary calciner.

In some embodiments, the method of making a microspherical fluid catalytic cracking catalyst consists essentially of the steps of mixing microspheres with a barium solution to form a barium-microsphere mixture; calcining the barium-microsphere mixture to form a first calcined material; mixing the first calcined material with an ammonium solution to form an ammoniated material; calcining the ammoniated material to form a second calcined material; and steam-treating the second calcined material. In some embodiments of the method, the microspheres include zeolite. In some embodiments of the method, the microspheres include Y-zeolite crystallized as a layer on the surface of a porous alumina-containing matrix. In further embodiments of the method, prior to the mixing, the microspheres are pre-treated to exchange sodium with ammonium ions. In some embodiments, cesium is used in place of barium.

In some embodiments of the method, the microspheres including zeolite undergo mixing in an ammonium solution and a first calcination prior to mixing with barium solution and undergoing a second calcination and steam treatment In further embodiments of the method, the microspheres are mixed with a second ammonium solution after the first calcination. In some embodiments, cesium is used in place of barium.

In some embodiments of the method, the microspheres including Y-zeolite crystallized as a layer on the surface of a porous alumina-containing matrix undergo mixing in an ammonium solution and a first calcination prior to mixing with barium solution and undergoing a second calcination and steam treatment In further embodiments of the method, the microspheres are mixed with a second ammonium solution after the first calcination. In some embodiments, cesium is used in place of barium.

In another aspect, disclosed herein are microspherical FCC catalysts as prepared by any of the methods disclosed herein.

Methods of Use

In another aspect, disclosed herein are methods to produce butylene in an FCC system, wherein the methods include using an FCC catalyst described herein.

In another aspect, disclosed herein are methods to improve butylene yield in an FCC system, wherein the methods include using an FCC catalyst described herein.

In another aspect, disclosed herein are methods to improve butylene selectivity in an FCC system, wherein the methods include using an FCC catalyst described herein.

In another aspect, disclosed herein are methods to lower coke production in an FCC system, wherein the methods include using an FCC catalyst described herein.

In another aspect, disclosed herein are methods to lower hydride transfer tendency in an FCC system, wherein the methods include using an FCC catalyst described herein.

The present invention, thus generally described, will be understood more readily by reference to the following examples, which are provided by way of illustration and are not intended to be limiting of the present invention.

EXAMPLES

Materials and Methods

Sodium-containing NAPHTHAMAX® was used as a starting material. Solutions of barium nitrate were made from crystalline material. Lab calcinations were conducted with 25% liquid water added to solid calcination feed in static air at 1150° F. for two hours. ASCII X-ray diffraction datasets containing ordered pairs of angle and intensity data were converted to General Structure Analysis System (GSAS) format and then Rietveld refined using GSAS driven by EXPGui (a graphical user interface for GSAS). The instrument function of the X-ray diffractometer was determined using a NIST SRM 660b $LaB_6$ specimen. Profile function type 2 is used to model lineshape; background may be modeled with Function type 1 or type 6. Use of these profile and background functions are discussed by Larson and Von Dreele in "General Structure Analysis System (GSAS)", Los Alamos National Laboratory Report LAUR 86-748, 2004. Steaming was conducted in fluidized beds at 1500° F. for four hours in 100% steam in open steamers. Catalytic cracking results were obtained using an ACE™ 1 reactor, gasoil feed, an injector height of 2.125", at about 1020° F. (548° C.).

Example 1. Preparation of Exemplary Barium-Containing Catalysts

Microspheres were made and Y-zeolite crystallized using methods described by Stockwell in U.S. Pat. No. 6,656,347, hereby incorporated by reference in its entirety. The resultant material, called NAPHTHAMAX®, contained Y-zeolite in the sodium form. Exchange with ammonium nitrate (pH 3, 80° C.) was then carried out and then the material was exchanged with barium nitrate solution. The material was filtered, dried, and calcined at 621° C. for two hours. The material was then exchanged again with ammonium nitrate (pH 3, 80° C. aqueous suspension), filtered, dried and calcined again at 621° C. for two hours. The amount of barium in the catalyst was varied by changing the concentration of barium in the barium nitrate solution. The twice-calcined catalyst was then deactivated with 100% steam in a fluidized bed reactor at 815° C. for 4 hours and then evaluated using a Constant Time On Stream protocol in a ACE™ reactor.

Example 2. Investigation of Zeolite Stability

Figure 2:
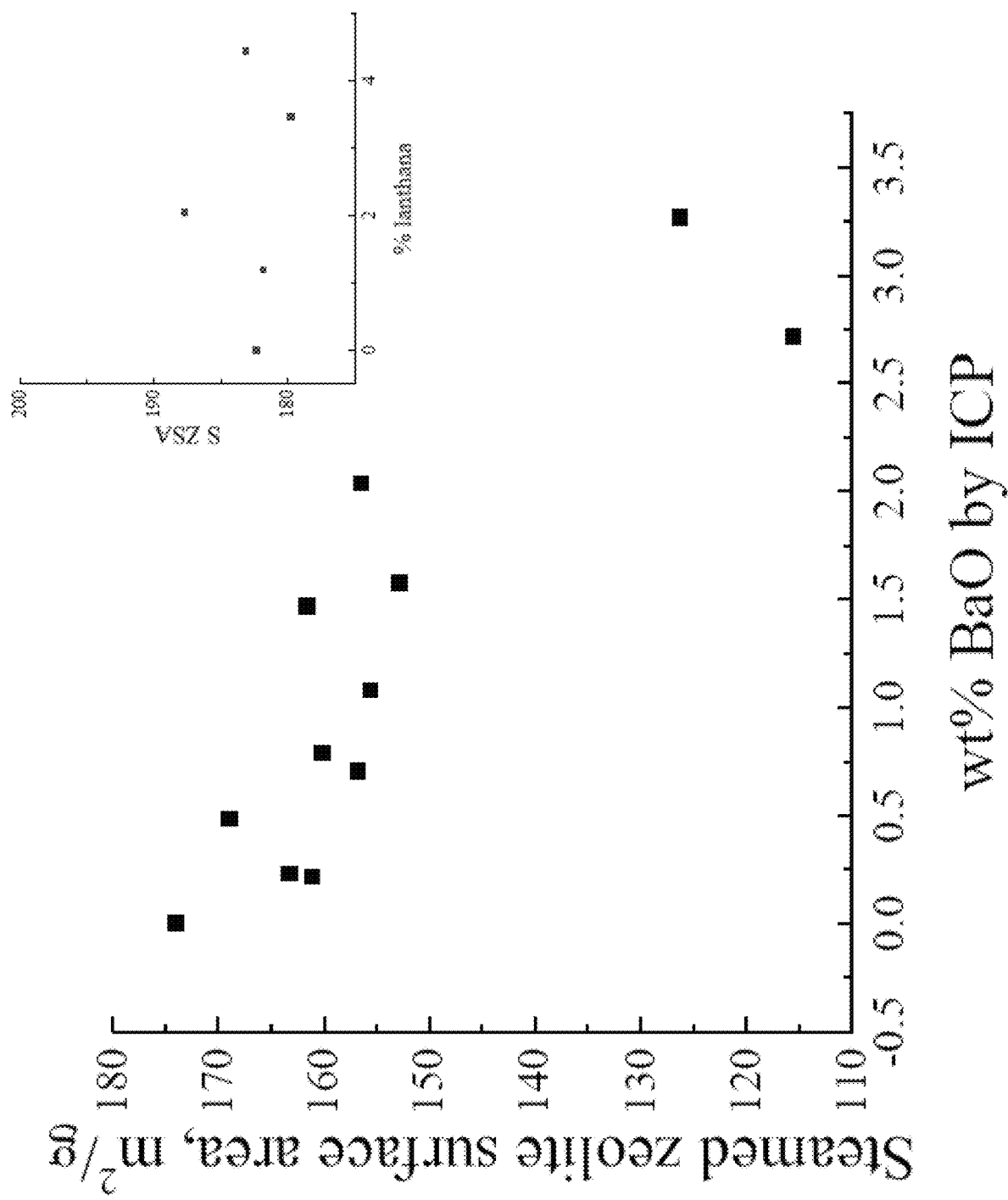
FIG. 2 illustrates surface area of steamed Y-zeolite as a function of barium content in barium-containing catalyst or, in inset graph, as a function of lanthanum content in lanthanum-containing catalyst.

Two sets of Ba-containing NAPHTHAMAX® materials were made from Na-NAPHTHAMAX® intermediate using the procedure in Example 1. The first set of materials had a range of barium content from 0.2 wt. % to 1.0 wt. %. As will be discussed below, these first materials were brought forward to finished products and their catalytic properties evaluated in the ACE™ reactor. A second set of materials was subsequently made with increased barium content. It was observed that Ba, at least when exchanged from nitrate solutions, destabilizes Y-zeolite. As barium content increased, steamed unit cell size and steamed zeolite surface area (ZSA) both decreased, as shown in FIGS. 1 and 2. Although barium in the zeolite does not occur as BaO, for experimental accounting purposes, barium is listed as BaO in FIG. 1, FIG. 2, and FIGS. 5-9. The inset in FIG. 1 shows the familiar stabilization of Y zeolite unit cell size by lanthanum. The inset in FIG. 2 shows that, consistent with commercial materials, steamed ZSA of lab-made lanthanum-containing NAPHTHAMAX® (La-NAPHTHAMAX®) was roughly constant with lanthana content. The behavior shown in FIG. 2, with lower ZSA as barium content increased, was in the same direction as would be expected for an alkali metal such as sodium. Apparently, barium has a modest activity for fluxing and destroying the zeolite.

Figure 3:
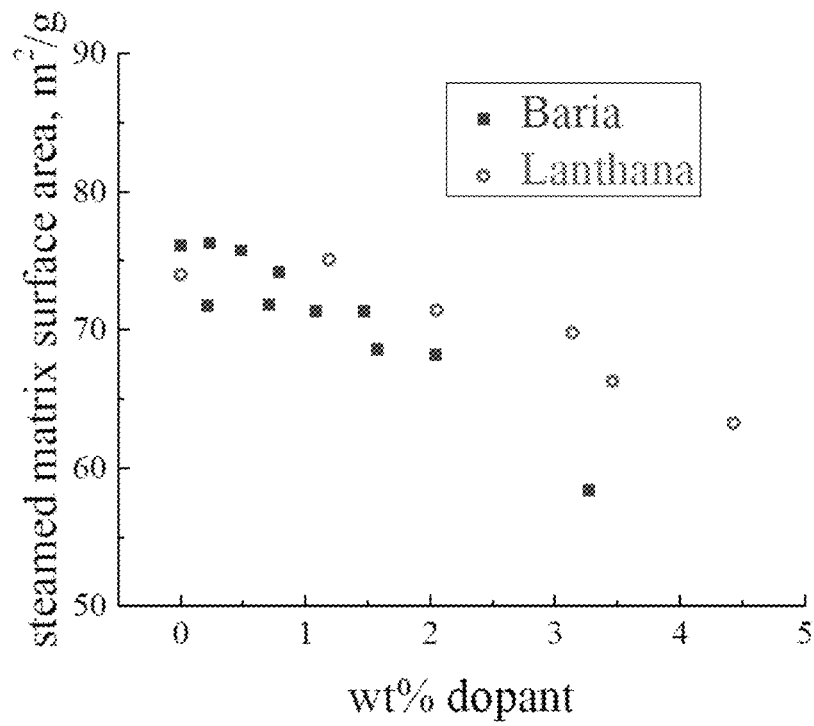
FIG. 3 illustrates steamed matrix surface area as a function of barium content in barium-containing catalyst.

Neither barium nor lanthanum stabilized matrix surface area, as shown in FIG. 3. Steamed matrix surface area showed a decreasing trend as either baria or lanthana content increased. This was surprising. NAPHTHAMAX® contains mullite, Y-zeolite, and engineered spinel. Engineered spinel is similar to $\gamma$-$Al_2O_3$ and is stabilized by silica. Both lanthana and baria are known to stabilize transitional alumina against loss of surface area caused by high temperature hydrothermal treatment. It is unlikely that the rather low steaming temperature (1500° F./815° C.) causes the engineered spinel to lose much surface area. With regard to NAPHTHAMAX®, a substantial portion of matrix surface area is associated with the zeolite rather than with matrix spinel. The fact that neither Ba nor La stabilized matrix surface area in a 815° C. steaming strongly suggested that most of this "matrix" is not associated with matrix alumina or mullite at all but instead is associated with zeolite external surfaces. Basic dopants, including baria and lanthana, appear to have a tendency to flux zeolite external area.

Example 4. Zeolite Structure

The 3.3 wt. % Ba-NAPHTHAMAX® catalyst was chosen for more detailed structural characterization using X-ray diffraction coupled with Rietveld analysis. Routine X-ray diffraction characterization reported that this material contained Y-zeolite, mullite, and anatase. The GSAS refinement yielded, at convergence, an estimate of Y-zeolite unit cell parameter of 24.2622±0.0011 Å that agreed well with the result obtained using ASTM method D3942 (24.25 Å). The difference in values is thought to arrive because specimens whose data were refined using GSAS were not hydrated while specimens whose data were analyzed based on method D3942 were hydrated, as per that method. Rietveld refinement can provide estimates of mass fractions of the crystalline portion of a sample but does not directly quantify amorphous material. Previous refinement work led to an adoption of an estimate of anatase content of 1.72 wt. % for these materials. Knowing the anatase content of the sample to be about 1.72 wt. %, and finding an apparent anatase mass fraction of this sample to be 3.91 wt. %, the mass fraction of mullite and Y zeolite was estimated. Mass fraction of zeolite was estimated from zeolite surface area. It is estimated that in-situ Y zeolite has a micropore surface area of about 660 $m^2/g$. Micropore surface area is the difference between the BET surface area and external surface area measured using the T-plot method. This estimate may also be used to estimate mass fraction of Y zeolite in a specimen: micropore surface area/660=mass fraction as estimated by BET measurements. An additional method to estimate zeolite mass fraction, the so-called ZI (Zeolite Index), based on ASTM method D3906 was also used, even though this method suffers from positive bias in the presence of mullite. With these methods three estimates of zeolite content were obtained: ZI, 25 wt. %; BET, 19 wt. %; and Rietveld, 16 wt. %.

Given the known bias, it was reasonable that the ZI estimate was highest: it should not be trusted. The BET and Rietveld estimates agreed well. Rietveld analysis indicated mullite content to be 26 wt. %. Rietveld analysis also indicated that 56 wt. % of the steamed 3.3 wt. % Ba-NAPHTHAMAX® was amorphous. Included in this amorphous matter was the $SiO_2$-stabilized $\gamma$-$Al_2O_3$ spinel that diffracts too weakly to be detected in this experiment.

Ultimately, Rietveld analysis was used to assess the location of barium ions. Rietveld refinement revealed lanthanum in steamed La-NAPHTHAMAX® occupied sites I' and II' in the sodalite cages. In steamed NAPHTHAMAX® without any exchanged cation, aluminum was found to occur at these sites. In as-crystallized Na-NAPHTHAMAX®, sodium occurred at sites II and III in the supercage and in sites I' and II'. These findings were all consistent with literature observations.

The refinement of barium occupancies at I', II', II, and III sites was performed separately and together. This analysis indicated that barium occupancies at sites I', II', and II were negative. This, of course, was physically impossible and indicated that barium did not occur at those sites. Unexpectedly, site III refined to slightly positive occupancy. Low occupancy can correspond to quite a bit of barium, though, since the multiplicity for site III is 96. The refinement indicated that about ⅓ of the total barium in the catalyst occurred at site III in the Y-zeolite supercages. This amounts to about 6 wt. % Ba in the zeolite that remains after steaming. Notably, Ba occupancy of site III has not been reported previously. Reflections of Y-zeolite were modeled unusually well in this refinement. Many refinement fit parameters were unusually good. The results showed that most of the barium was not in the zeolite. It is known that barium hydroxide can be mobile in the presence of steam at elevated temperatures. The steaming temperature (815° C.) in these experiments was warm enough that mobility likely occurred. A substantial portion of the barium may have occurred on silica-alumina amorphous material rather than on the Y-zeolite.

Example 5. Catalytic Properties

Having shown that ion exchange of barium, in place of lanthanum, into the Y-zeolite of NAPHTHAMAX® resulted in quite different physicochemical consequences, catalytic results obtained in the ACE™ reactor were investigated.

Figure 4:
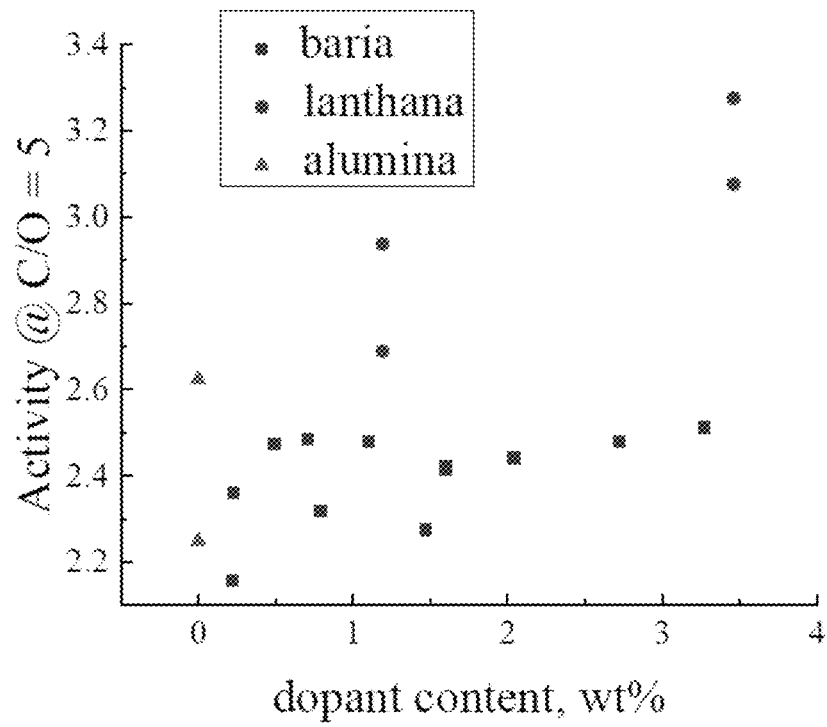
FIG. 4 illustrates estimated activity at catalyst/oil=5 as a function of dopant content.

Ba-containing NAPHTHAMAX® was less active than La-containing analogs. FIG. 4 illustrates second-order activity at catalyst/oil (C/O)=5 for results from two ACE™ campaigns. The two lanthana controls used in each ACE™ experiment were, in fact, the same type of materials which underwent the same steaming conditions. Those controls suggested that the results from one campaign are about 9% more active than the results of the other. This variation of activity with time did not affect the observation that the baria catalysts were less active than the lanthana catalysts. The activity variation, though, does make ambiguous whether baria catalysts were more active than catalysts for which no metal cation was used. In FIG. 4, catalysts where no metal cation was exchanged was labelled as "alumina". This "alumina" material was less active than all of the baria-containing materials. On the other hand, the "alumina" material evaluated in another experiment was a bit more active than all the baria-containing materials. Consequently, it is unclear if Ba-containing NAPHTHAMAX® is more or less active than dopant-free NAPHTHAMAX®.

Figure 5:
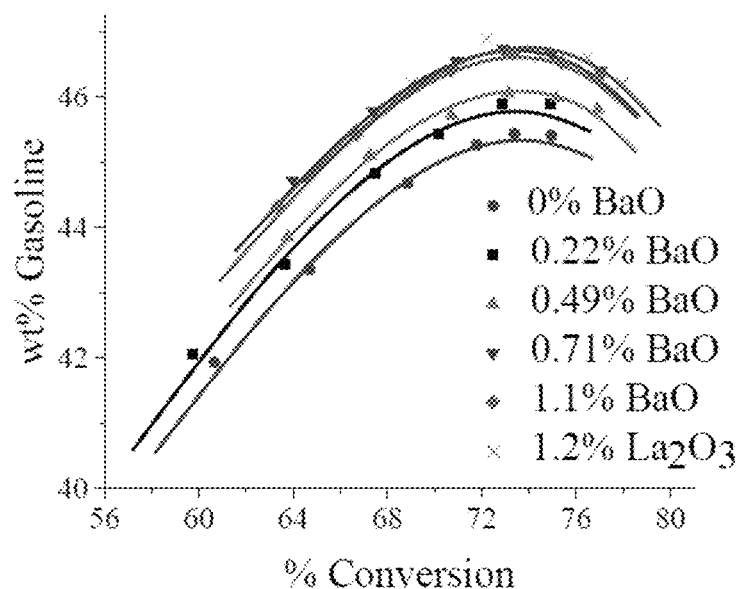
FIG. 5 illustrates gasoline selectivity with catalysts containing 0.7-1.1 wt. % barium compared to a 1.4 wt. % lanthana control catalyst.

FIG. 5 shows that catalysts with barium contents of 0.7-1.1 wt. % had similar gasoline selectivities to a 1.2 wt. % $La_2O_3$ control catalyst. The 3.5 wt. % lanthana control (not shown) made about 1% more gasoline than the 1.2 wt. % lanthana control. With respect to gasoline production, these baria-containing catalysts clearly were not superior to a 3 wt. % lanthana reference. Compared to the 1.2 wt. % lanthana control, these baria-containing catalysts made 0.4% more to 0.2% less coke, on an relative basis. These low baria-containing catalysts had equivalent coke selectivity to 1.2 wt. % $La_2O_3$-NAPHTHAMAX®.

Figure 6:
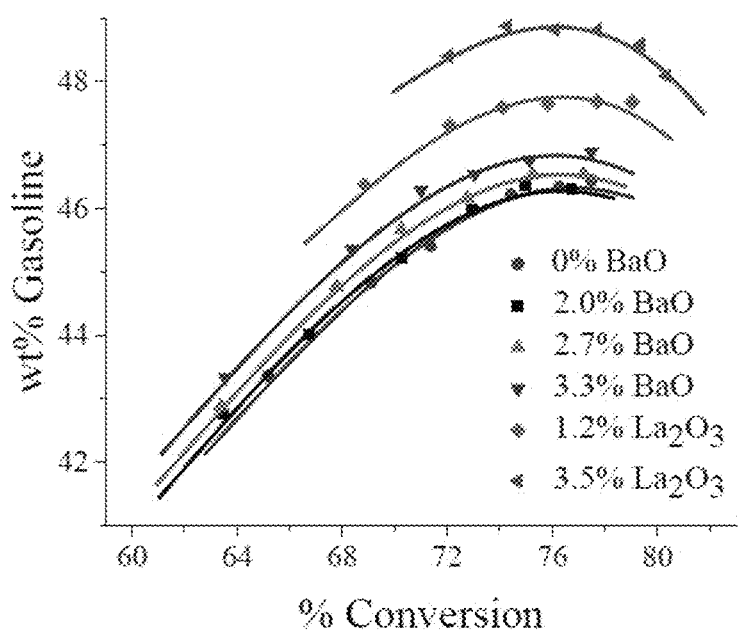
FIG. 6 illustrates gasoline selectivity with catalysts containing 2.0-3.3 wt. % barium compared to a 1.2 wt. % or 3.5 wt. % lanthana control catalyst.
Figure 7:
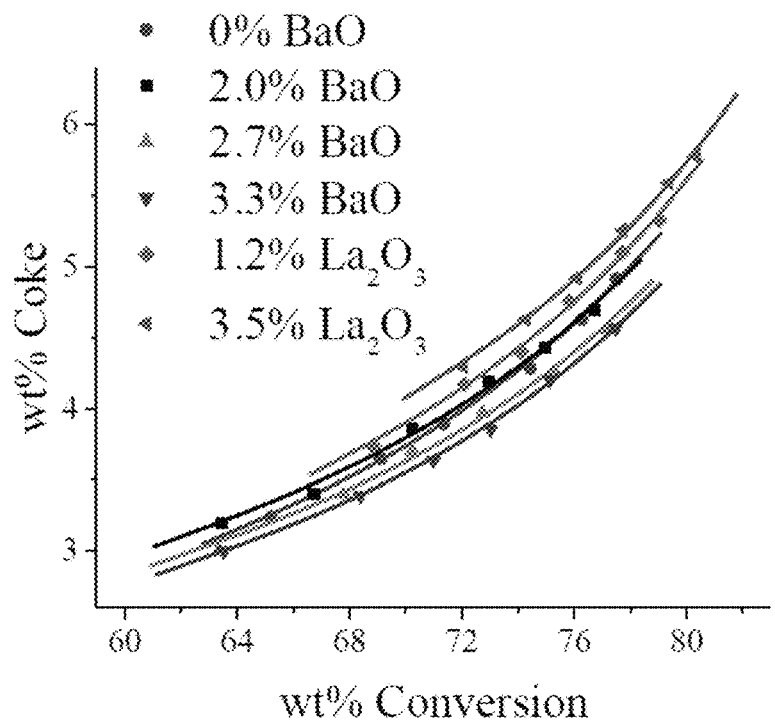
FIG. 7 illustrates coke selectivity for barium-containing catalysts compared with lanthanum-containing catalysts.

Performance with higher baria content was also assessed. Select gasoline yield results for this experiment are shown in FIG. 6. In this experiment, the lanthana catalysts performed relatively better. For example, 3.3 wt. % Ba-NAPHTHAMAX® had a 2 wt. % decrease in gasoline yield compared to the 3.5 wt. % La-NAPHTHAMAX®. The baria catalysts also had gasoline selectivities inferior to or similar (not shown) to a catalyst free of baria and lanthana. On the other hand, the baria-containing catalysts made less coke (see FIG. 7). Catalysts containing 3.3 wt. % baria made about 12% less coke than 3.5 wt. % La-NAPHTHAMAX®. However, at lower baria content, a coke advantage was not observed. These experiments indicated that the largest coke benefits occurred when baria content was about 3 wt. %, such catalysts making 0.3-0.6 wt. % more gasoline and about 7 wt. % less coke than a catalyst with no exchanged cation.

Figure 8:
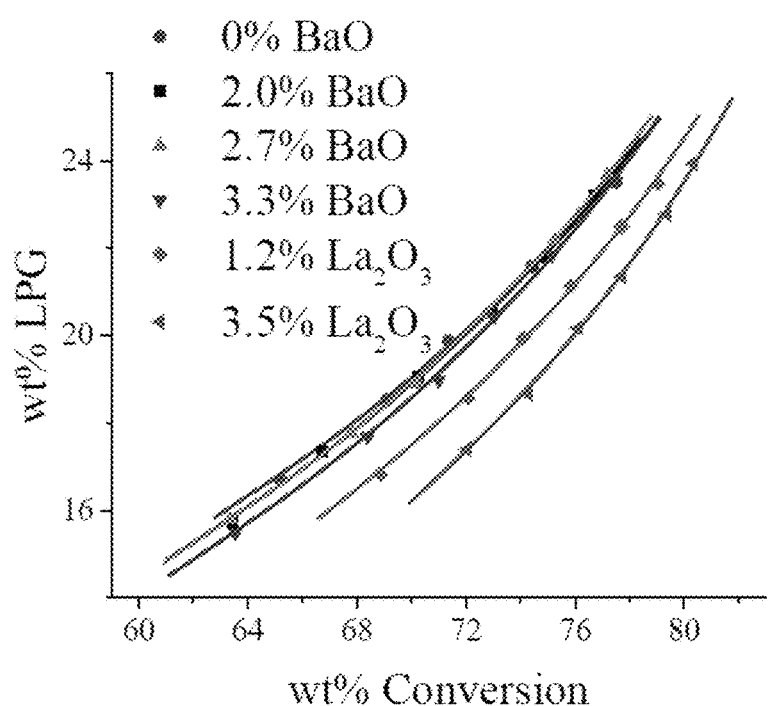
FIG. 8 illustrates production of liquefied petroleum gas (LPG) at a given conversion for barium- or lanthanum-containing catalysts.

Overall LPG production was also assessed. Moreover, GC data acquired from these ACE experiments enabled an assessment of olefinicity. FIG. 8 shows that 2-3 wt. % baria catalysts make more LPG than either 1.2 or 3.5 wt. % La-NAPHTHAMAX®. While a catalyst with neither baria nor lanthana has similar LPG advantages, that catalyst makes more coke than the baria catalysts.

Figure 9:
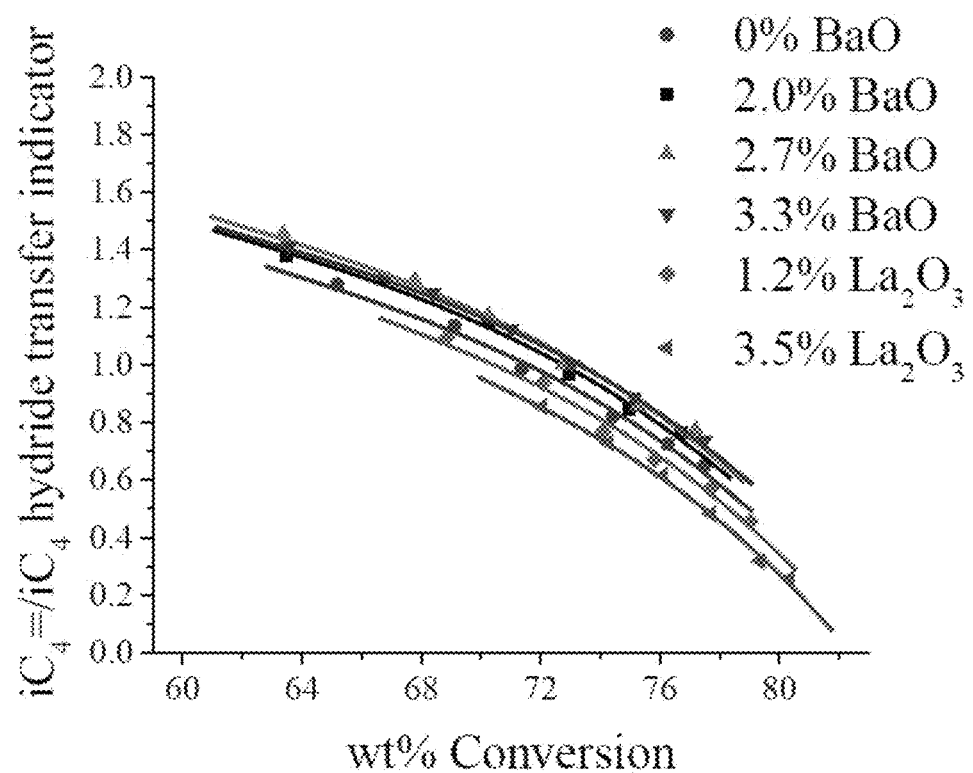
FIG. 9 illustrates isobutene/isobutane ratios as a function of conversion for barium- or lanthanum-containing catalysts.

Baria-containing catalysts show substantially higher isobutene/isobutane ratios than La-NAPHTHAMAX®, as shown in FIG. 9. Ba-NAPHTHAMAX® had higher isobutene/isobutene ratios than catalysts with neither Ba nor La as exchange cations. The isobutene/isobutene ratio is diagnostic of hydride transfer strength. Baria catalysts had rather low hydride transfer capabilities. The baria catalysts made more propylene, ethylene and about 0.8-1% more n-butenes than lanthana catalysts. These considerations all support the assertion that baria catalysts made a more olefinic product.

Para. A. A microspherical fluid catalytic cracking catalyst comprising Y-zeolite and barium ion.

Para. B. The catalyst of Para. A, wherein the catalyst has an average particle size of from about 60 to about 100 micrometers.

Para. C. The catalyst of Para. A or Para. B, wherein the catalyst has an average particle size of from about 60 to about 80 micrometers.

Para. D. The catalyst of Para. A or Para. B, wherein the catalyst has an average particle size of about 70 to about 90 micrometers.

Para. E. The catalyst of any one of Paras. A-D, wherein the catalyst has a phase composition comprising at least about 10 wt. % Y-zeolite.

Para. F. The catalyst of any one of Paras. A-D, wherein the catalyst has a phase composition comprising at least about 15 wt. % Y-zeolite.

Para. G. The catalyst of any one of Paras. A-D, wherein the catalyst has a phase composition comprising at least about 18 wt. % Y-zeolite.

Para. H. The catalyst of any one of Paras. E-G, wherein the phase composition further comprises at least about 30 wt. % amorphous material.

Para. I. The catalyst of any one of Paras. E-G, wherein the phase composition further comprises at least about 40 wt. % amorphous material.

Para. J. The catalyst of any one of Paras. E-G, wherein the phase composition further comprises at least about 50 wt. % amorphous material.

Para. K. The catalyst of any one of Paras. H-J, wherein the amorphous material comprises silica-alumina.

Para. L. The catalyst of any one of Paras. E-K, wherein the phase composition further comprises at least about 20 wt. % mullite.

Para. M. The catalyst of any one of Paras. E-K, wherein the phase composition further comprises at least about 30 wt. % mullite.

Para. N. The catalyst of any one of Paras. A-M, wherein the Y-zeolite has a unit cell parameter of from about 24.10 Å to about 24.7.0 Å.

Para. O. The catalyst of any one of Paras. A-N, wherein the Y-zeolite has a unit cell parameter of from about 24.45 Å to about 24.51 Å.

Para. P. The catalyst of any one of Paras. A-O, wherein the Y-zeolite unit cell comprises barium ion at the ion exchange site III.

Para. Q. The catalyst of any one of Paras. A-P, wherein the Y-zeolite unit cell comprises 4 barium atoms at the ion exchange site III.

Para. R. The catalyst of any one of Paras. A-Q, wherein no more than about half of the barium ions can be located on the Y-zeolite by x-ray diffraction.

Para. S. The catalyst of any one of Paras. A-R, wherein the barium ions do not occupy ion exchange sites I' and II' of the Y-zeolite unit cell.

Para. T. The catalyst of any one of Paras. A-S, wherein the catalyst comprises at least about 2 wt. % barium ion.

Para. U. The catalyst of any one of Paras. A-T, wherein the catalyst comprises at least about 3 wt. % barium ion.

Para. V. The catalyst of any one of Paras. A-U, wherein the Y-zeolite is crystallized as a layer on the surface of a porous alumina-containing matrix.

Para. W. The catalyst of Para. V, wherein the matrix is derived from a kaolin calcined through the exotherm.

Para. X. A microspherical catalyst comprising about 3.3 wt. % barium ion, wherein the catalyst has a phase composition comprising about 18 wt. % Y-zeolite, about 30 wt. % mullite, about 2 wt. % anatase, and about 50 wt. % amorphous material.

Para. Y. The catalyst of Para. X, wherein the Y-zeolite has a unit cell parameter of about 24.26 Å.

Para. Z. The catalyst of Para. X or Para. Y, wherein the catalyst contains about 4 barium atoms in the Y zeolite unit cell at ion exchange site III.

Para. AA. The catalyst of Para. Z, wherein the fractional coordinates of ion exchange site III are $x=y=0.35$ and $z=0.21$.

Para. AB. The catalyst of any one of Paras. X-AA, wherein only about half of the barium ions can be located in the zeolite by X-ray diffraction.

Para. AC. The catalyst of any one of Paras. X-AB, wherein the catalyst has an average particle size of 60-80 micrometers.

Para. AD. A method of making a microspherical fluid catalytic cracking catalyst,
the method comprising:
mixing microspheres with a barium solution to form a barium-microsphere mixture; and
calcining the barium-microsphere mixture to form a first calcined material;
wherein:
prior to the mixing with the barium solution, the microspheres comprise Y-zeolite crystallized as a layer on the surface of a porous alumina-containing matrix.

Para. AE. The method of Para. AD, wherein the mixing with the barium solution is conducted at acidic pH conditions.

Para. AF. The method of Para. AD or Para. AE, wherein the mixing with the barium solution is conducted at pH=3.

Para. AG. The method of any one of Paras. AD-AF, wherein the mixing with the barium solution is conducted at a temperature above room temperature.

Para. AH. The method of any one of Paras. AD-AG, wherein the mixing with the barium solution is conducted at a temperature of at least about 50° C.

Para. AI. The method of any one of Paras. AD-AG, wherein the mixing with the barium solution is conducted at a temperature of about 80° C.

Para. AJ. The method of any one of Paras. AD-AI, wherein calcining the barium-microsphere mixture is conducted for at least about 15 minutes.

Para. AK. The method of any one of Paras. AD-AI, wherein calcining the barium-microsphere mixture is conducted for at least about one hour.

Para. AL. The method of any one of Paras. AD-AI, wherein calcining the barium-microsphere mixture is conducted for at least about two hours.

Para. AM. The method of any one of Paras. AD-AL, wherein calcining the barium-microsphere mixture is conducted at a temperature of from about 500° C. to about 700° C.

Para. AN. The method of any one of Paras. AD-AM, further comprising mixing the microspheres with an ammonium solution prior to the mixing with the barium solution, wherein the microspheres comprise Y-zeolite in the sodium form prior to the mixing with the ammonium solution.

Para. AO. The method of Para. AN, wherein the mixing with the ammonium solution is conducted at acidic pH conditions.

Para. AP. The method of Para. AN or Para. AO, wherein the mixing with the ammonium solution is conducted at pH=3.

Para. AQ. The method of any one of Paras. AN-AP, wherein the mixing with the ammonium solution is conducted at a temperature above room temperature.

Para. AR. The method of any one of Paras. AN-AQ, wherein the mixing with the ammonium solution is conducted at a temperature of at least about 50° C.

Para. AS. The method of any one of Paras. AN-AQ, wherein the mixing with the ammonium solution is conducted at a temperature of about 80° C.

Para. AT. The method of any one of Paras. AN-AS, further comprising mixing the first calcined material with another ammonium solution to form an ammoniated material.

Para. AU. The method of Para. AT, wherein the mixing with another ammonium solution is conducted at acidic pH conditions.

Para. AV. The method of Para. AT or Para. AU, wherein the mixing with another ammonium solution is conducted at pH=3.

Para. AW. The method of any one of Paras. AT-AV, wherein the mixing with another ammonium solution is conducted at a temperature above room temperature.

Para. AX. The method of any one of Paras. AT-AW, wherein the mixing with another ammonium solution is conducted at a temperature of at least about 50° C.

Para. AY. The method of any one of Paras. AT-AW, wherein the mixing with another ammonium solution is conducted at a temperature of about 80° C.

Para. AZ. The method of any one of Paras. AT-AY, further comprising calcining the ammoniated material to form a second calcined material.

Para. BA. The method of Para. AZ, wherein calcining the ammoniated material is conducted for at least about 15 minutes.

Para. BB. The method of Para. AZ, wherein calcining the ammoniated material is conducted for at least about one hour.

Para. BC. The method of Para. AZ, wherein calcining the ammoniated material is conducted for at least about two hours.

Para. BD. The method of any one of Paras. AZ-BC, wherein calcining the ammoniated material is conducted at a temperature of from about 500° C. to about 700° C.

Para. BE. The method of any one of Paras. AD-BD, further comprising steam-treating.

Para. BF. The method of Para. BE, wherein the steam-treating is conducted at a temperature of at least about 600° C.

Para. BG. The method of Para. BE, wherein the steam-treating is conducted at a temperature of at least about 700° C.

Para. BH. The method of Para. BE, wherein the steam-treating is conducted at a temperature of at least about 800° C.

Para. BI. The method of any one of Paras. BE-BH, wherein the steam-treating is conducted for at least about two hours.

Para. BJ. The method of any one of Paras. BE-BH, wherein the steam-treating is conducted for at least about three hours.

Para. BK. The method of any one of Paras. BE-BH, wherein the steam-treating is conducted for at least about four hours.

Para. BL. The method of any one of Paras. BE-BK, wherein the steam-treating is conducted in a fluidized bed reactor.

Para. BM. A microspherical fluid catalytic cracking catalyst as prepared by any one of Paras. AD-BL.

Para. BN. A microspherical fluid catalytic cracking catalyst comprising Y-zeolite and barium ion.

Para. BO. The catalyst of Para. BN, wherein the catalyst has an average particle size of from about 60 to about 100 micrometers, or from about 60 to about 80 micrometers, or from about 70 to about 90 micrometers.

Para. BP. The catalyst of Para. BN or Para. BO, wherein the catalyst has a phase composition comprising at least about 10 wt. % Y-zeolite, or at least about 15 wt. % Y-zeolite, or at least about 18 wt. % Y-zeolite.

Para. BQ. The catalyst of Para. BP, wherein the phase composition further comprises at least about 30 wt. % amorphous material, or at least about 40 wt. % amorphous material, or at least about 50 wt. % amorphous material.

Para. BR. The catalyst of Para. BQ, wherein the amorphous material comprises silica-alumina.

Para. BS. The catalyst of any one of Paras. BP-BR, wherein the phase composition further comprises at least about 20 wt. % mullite or at least about 30 wt. % mullite.

Para. BT. The catalyst of any one of Paras. BN-PS, wherein the Y-zeolite has a unit cell parameter of from about 24.10 Å to about 24.7.0 Å, or from about 24.45 Å to about 24.51 Å.

Para. BU. The catalyst of any one of Paras. BN-BT, wherein the Y-zeolite unit cell comprises barium ion at the ion exchange site III.

Para. BV. The catalyst of any one of Paras. BN-BU, wherein the Y-zeolite unit cell comprises 4 barium atoms at the ion exchange site III.

Para. BW. The catalyst of any one of Paras. BN-BV, wherein no more than about half of the barium ions can be located on the Y-zeolite by x-ray diffraction.

Para. BX. The catalyst of any one of Paras. BN-BW, wherein the barium ions do not occupy ion exchange sites I' and II' of the Y-zeolite unit cell.

Para. BY. The catalyst of any one of Paras. BN-BX, wherein the catalyst comprises at least about 2 wt. % barium ion, or at least about 3 wt. % barium ion.

Para. BZ. The catalyst of any one of Paras. BN-BY, wherein the Y-zeolite is crystallized as a layer on the surface of a porous alumina-containing matrix.

Para. CA. The catalyst of Para. BZ, wherein the matrix is derived from a kaolin calcined through the exotherm.

Para. CB. A microspherical catalyst comprising about 3.3 wt. % barium ion, wherein the catalyst has a phase composition comprising about 18 wt. % Y-zeolite, about 30 wt. % mullite, about 2 wt. % anatase, and about 50 wt. % amorphous material.

Para. CC. The catalyst of Para. CB, wherein the Y-zeolite has a unit cell parameter of about 24.26 Å.

Para. CD. The catalyst of Para. CB or Para. CC, wherein the catalyst contains about 4 barium atoms in the Y zeolite unit cell at ion exchange site III.

Para. CE. The catalyst of Para. CD, wherein the fractional coordinates of ion exchange site III are x=y=0.35 and z=0.21.

Para. CF. The catalyst of any one of Paras. CB-CE, wherein only about half of the barium ions can be located in the zeolite by X-ray diffraction.

Para. CG. The catalyst of any one of Paras. CB-CF, wherein the catalyst has an average particle size of 60-80 micrometers.

Para. CH. A method of making a microspherical fluid catalytic cracking catalyst,
the method comprising:
  mixing microspheres with a barium solution to form a barium-microsphere mixture; and
  calcining the barium-microsphere mixture to form a first calcined material;
wherein:
prior to the mixing with the barium solution, the microspheres comprise Y-zeolite crystallized as a layer on the surface of a porous alumina-containing matrix.

Para. CI. The method of Para. CH, wherein the mixing with the barium solution is conducted at acidic pH conditions.

Para. CJ. The method of Para. CH or Para. CI, wherein the mixing with the barium solution is conducted at pH=3.

Para. CK. The method of any one of Paras. CH-CJ, wherein the mixing with the barium solution is conducted at a temperature above room temperature, or at a temperature of at least about 50° C., or at a temperature of about 80° C.

Para. CL. The method of any one of Paras. CH-CK, wherein calcining the barium-microsphere mixture is conducted for at least about 15 minutes, or at least about one hour, or at least about two hours.

Para. CM. The method of any one of Paras. CH-CL, wherein calcining the barium-microsphere mixture is conducted at a temperature of from about 500° C. to about 700° C.

Para. CN. The method of any one of Paras. CH-CM, further comprising mixing the microspheres with an ammonium solution prior to the mixing with the barium solution, wherein the microspheres comprise Y-zeolite in the sodium form prior to the mixing with the ammonium solution.

Para. CO. The method of Para. CN, wherein the mixing with the ammonium solution is conducted at acidic pH conditions.

Para. CP. The method of Para. CN or Para. CO, wherein the mixing with the ammonium solution is conducted at pH=3.

Para. CQ. The method of any one of Paras. CN-CP, wherein the mixing with the ammonium solution is conducted at a temperature above room temperature, or at a temperature of at least about 50° C., or at a temperature of about 80° C.

Para. CR. The method of any one of Paras. CH-CQ, further comprising mixing the first calcined material with another ammonium solution to form an ammoniated material.

Para. CS. The method of Para. CR, wherein the mixing with another ammonium solution is conducted at acidic pH conditions.

Para. CT. The method of Para. CR or Para. CS, wherein the mixing with another ammonium solution is conducted at pH=3.

Para. CU. The method of any one of Paras. CR-CT, wherein the mixing with another ammonium solution is conducted at a temperature above room temperature, or at a temperature of at least about 50° C., or at a temperature of about 80° C.

Para. CV. The method of any one of Paras. CR-CU, further comprising calcining the ammoniated material to form a second calcined material.

Para. CW. The method of Para. CV, wherein calcining the ammoniated material is conducted for at least about 15 minutes, or at least about one hour, or at least about two hours.

Para. CX. The method of Para. CV or Para. CW, wherein calcining the ammoniated material is conducted at a temperature of from about 500° C. to about 700° C.

Para. CY. The method of any one of Paras. CH-CX, further comprising steam-treating.

Para. CZ. The method of Para. CY, wherein the steam-treating is conducted at a temperature of at least about 600° C., or at least about 700° C., or at least about 800° C.

Para. DA. The method of Para. CY or Para. CZ, wherein the steam-treating is conducted for at least about two hours, or at least about three hours, or at least about four hours.

Para. DB. The method of any one of Paras. CY-DA, wherein the steam-treating is conducted in a fluidized bed reactor.

Para. DC. A microspherical fluid catalytic cracking catalyst as prepared by any one of Paras. CH-DB.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A method of making a microspherical fluid catalytic cracking catalyst, the method comprising:
   mixing microspheres with a barium solution to form a barium-microsphere mixture; and
   calcining the barium-microsphere mixture to form a first calcined material;
   wherein:
   prior to the mixing with the barium solution, the microspheres comprise Y-zeolite crystallized as a layer on the surface of a porous alumina-containing matrix; and
   the mixing with the barium solution is conducted at acidic pH conditions.

2. The method of claim 1, wherein the mixing with the barium solution is conducted at pH=3.

3. The method of claim 1, wherein the mixing with the barium solution is conducted at a temperature above room temperature.

4. The method of claim 1, wherein calcining the barium-microsphere mixture is conducted for at least about 15 minutes.

5. The method of claim 1, wherein calcining the barium-microsphere mixture is conducted at a temperature of from about 500° C. to about 700° C.

6. The method of claim 1, further comprising mixing the microspheres with an ammonium solution prior to the mixing with the barium solution, wherein the microspheres comprise Y-zeolite in the sodium form prior to the mixing with the ammonium solution.

7. The method of claim 6, wherein the mixing with the ammonium solution is conducted at acidic pH conditions.

8. The method of claim 6, wherein the mixing with the ammonium solution is conducted at pH=3.

9. The method of claim 6, wherein the mixing with the ammonium solution is conducted at a temperature above room temperature.

10. The method of claim 1, further comprising mixing the first calcined material with another ammonium solution to form an ammoniated material.

11. The method of claim 10, wherein the mixing with another ammonium solution is conducted at acidic pH conditions.

12. The method of claim 10, wherein the mixing with another ammonium solution is conducted at pH=3.

13. The method of claim 10, wherein the mixing with another ammonium solution is conducted at a temperature above room temperature.

14. The method of claim 10, further comprising calcining the ammoniated material to form a second calcined material.

15. The method of claim 14, wherein calcining the ammoniated material is conducted for at least about 15 minutes.

16. The method of claim 14, wherein calcining the ammoniated material is conducted at a temperature of from about 500° C. to about 700° C.

17. The method of claim 1, further comprising steam-treating.

18. The method of claim 17, wherein the steam-treating is conducted at a temperature of at least about 600° C.

19. The method of claim 17, wherein the steam-treating is conducted for at least about two hours.

20. The method of claim 17, wherein the steam-treating is conducted in a fluidized bed reactor.

21. The method of claim 1, wherein the microspherical fluid catalytic cracking catalyst comprises Y-zeolite comprising a Y-zeolite unit cell having an ion exchange site III, and the Y-zeolite unit cell comprises barium ion at the ion exchange site III.

\* \* \* \* \*